US00PP37162P2

(12) United States Plant Patent
Korlipara

(10) Patent No.: US PP37,162 P2
(45) Date of Patent: Dec. 16, 2025

(54) ***RUDBECKIA* PLANT NAMED 'Summer Sienna'**

(50) Latin Name: *Rudbeckia hirta*
Varietal Denomination: Summer Sienna

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/897,587

(22) Filed: Sep. 26, 2024

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

PUBLICATIONS https://1grmag.com/news/terra-nova-nurseries-to-debut-new-introductions-catalog-at-cultivate23/ (Retrieved online Dec. 18, 2024) (Year: 2023).*

* cited by examiner

*Primary Examiner* — Shubo Zhou
*Assistant Examiner* — Zachariah Allan Kay
(74) *Attorney, Agent, or Firm* — Klarquist Sparkman, LLP

(57) ABSTRACT

A new and distinct *Rudbeckia hirta* plant named 'Summer Sienna' characterized by its semi double inflorescence with deep orange yellow and dark red ray florets, medium rounded upright growth habit, and excellent vigor from spring through fall.

2 Drawing Sheets

Latin name of the genus and species of the plant claimed: *Rudbeckia hirta.*

Variety designation: 'Summer Sienna'.

BACKGROUND

The present invention relates to a new and distinct cultivar of *Rudbeckia hirta* named 'Summer Sienna'. *Rudbeckia* is in the family Asteraceae. This new cultivar is a selection from a planned breeding program performed in Canby, Oregon USA. Both parents are unnamed, unpatented, proprietary seedlings. The seed parent is a proprietary *Rudbeckia hirta* seedling (Rh 20-6), semi-double with yellow to orange petals and large habit and the pollen parent is a *Rudbeckia hirta* seedling (Rh 18-7) with semi double dark brown flowers and a short habit.

SUMMARY

The new *Rudbeckia* cultivar 'Summer Sienna' is distinguished from other *Rudbeckia* varieties due to the following unique combination of characteristics:

1. Inflorescence with semi double ray florets, and
2. Medium, upright and rounded habit, and Compared to 'Summer Sienna', the seed parent is taller and more upright with larger flowers. Compared to the pollen parent, 'Summer Sienna' has more crowns and more numerous flowers that are held on well branched scapes.

'Summer Sienna' is distinct from other known *Rudbeckia* varieties, for example, 'Goldsturm' (unpatented), 'Henry Eilers', (unpatented), and 'BullRudihir 119' (U.S. Plant Pat. No. 35,871). Compared to 'Goldsturm', 'Summer Sienna' has semi-double flowers rather than single flowers. Compared to 'Henry Eilers', 'Summer Sienna' has semi-double flowers and is much shorter, with better branching. Compared to 'BullRudihir 119', 'Summer Sienna' has many more branches, is broader and has semi-double flowers (not single flowers) in mixed colors of burnt umber and sienna.

The new cultivar has been reproduced only by asexual propagation (cuttings and tissue culture), beginning in Summer of 2022 at a nursery in Canby, Oregon USA. Each of the progeny exhibits identical characteristics to the original plant. Asexual propagation by cuttings and tissue culture using standard micropropagation techniques with terminal and lateral shoots, as done in Canby, Oregon, shows that the characteristics described herein come true to form, are firmly fixed, and are established and transmitted through succeeding propagations.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to *The Royal Horticultural Society Colour Chart,* $5^{th}$ edition, 2007.

Figure 1:
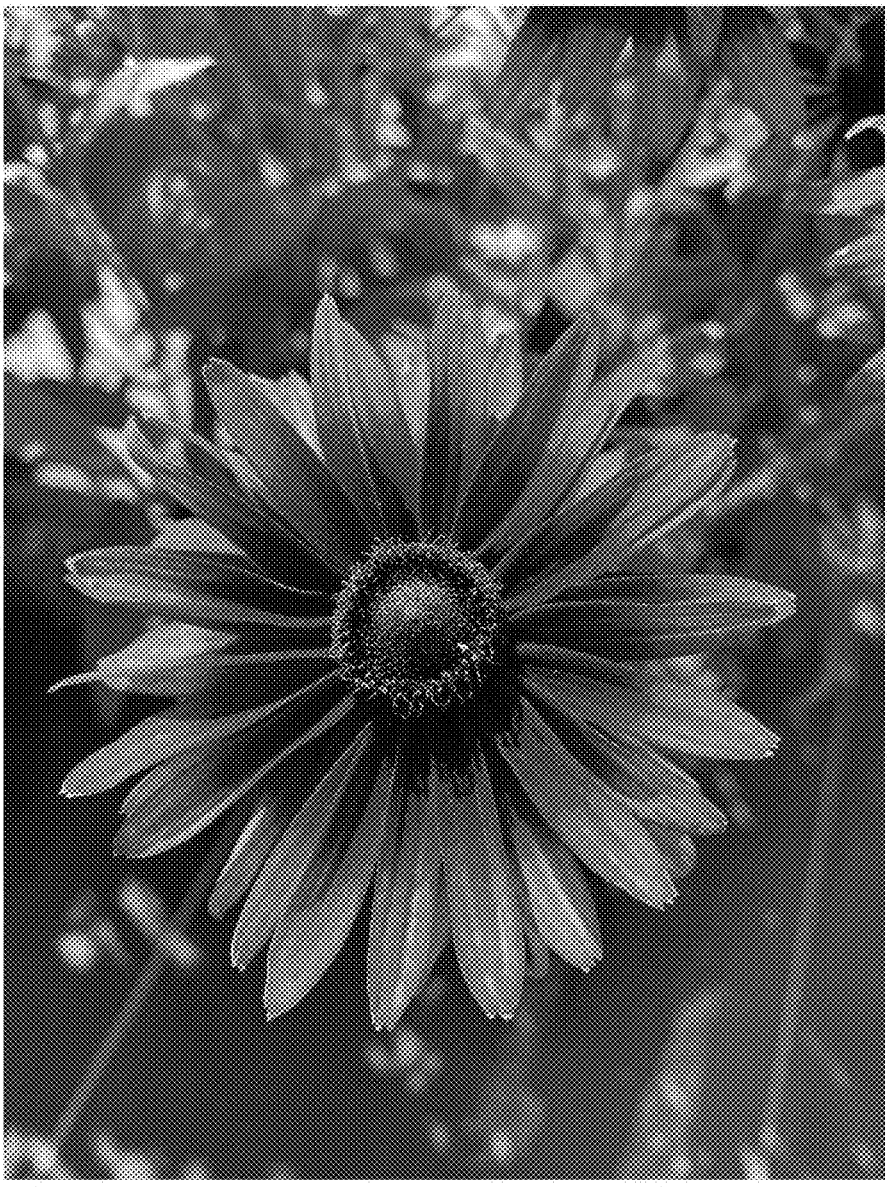
FIG. 1 shows a close up of an inflorescence of a 9-month old *Rudbeckia* 'Summer Sienna'.
Figure 2:
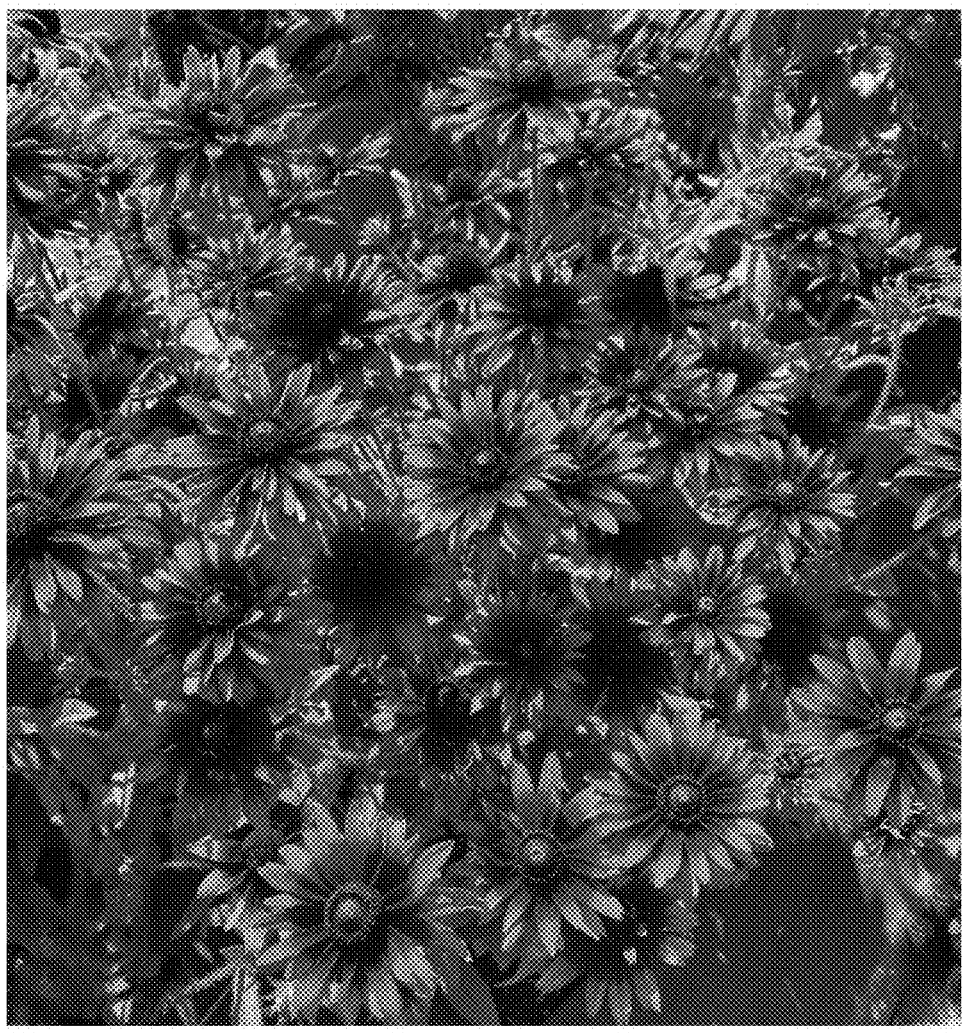
FIG. 2 shows the original 9-month old plant in the field of a nursery in full sun in early July in Canby, Oregon.

The color photographs show typical specimens of the new cultivar and depict the color as nearly true as is reasonably possible. It should be noted that colors may vary, for example due to lighting conditions at the time the photograph is taken. Therefore, color characteristics of this new cultivar should be determined with reference to the observations described herein, rather than from the photograph alone.

DETAILED PLANT DESCRIPTION

The following detailed description of the new *Rudbeckia* cultivar is based on observations of 6-month-old asexually reproduced specimens growing in a garden in full sun in Canby, Oregon. Canby is in Zone 8 on the USDA Hardiness map. Temperatures range from a high of 95° F. in August to an average of 32° F. in January. Normal rainfall in Canby is 42.8 inches per year.

Plant:

*Type*.—Herbaceous annual.

*Hardiness*.—USDA Zones annual.

*Size*.—Grows to about 65 cm wide and 56 cm tall to top of inflorescences.

*Form*.—Basal clump, with about 18 stems from the base.

Stem (flowering):

*Type*.—Ascending, branching where flowering only, with 10 to 14 flowers per stem.

*Size*.—Up to 13 cm tall to the start of a flowering branch, 3 to 3.5 mm wide at the base.

*Internode length*.—4 cm to 5 cm.

*Surface texture*.—Strigose.

*Color*.—Yellow-green 145A upper with 144A near base.

Leaf (stem):

*Type*.—Simple.

*Shape*.—Lanceolate.

*Arrangement*.—Alternate, occasionally whorled in threes.

*Blade size*.—Grows overall to 18 cm long and 3.5 cm wide, terminal leaflet grows to 7.5 cm long and 2.5 cm wide, lateral leaflets grow to 5 cm long and 2 cm wide.

*Margins*.—Serrate.

*Apex*.—Acute.

*Base*.—Attenuate.

*Surface texture*.—Strigose on both sides.

*Venation*.—Pinnate, with 3 main veins from the base on each leaflet.

*Color*.—Topside green 137C, veins green 137C, bottom side green 147B.

*Petiole description*.—Grows to 1 cm long and 4 mm wide above the clasp, strigose, yellow green 146D.

Inflorescence:

*Type*.—Composite.

*Number of flowering branches from stem*.—5 to 7.

*Flowering stem*.—Grows to 45 cm tall from the start of the flowering branches to the base of the terminal inflorescence and the 5 to 10 side branches grow 10 to 17 cm taller than the terminal; peduncle to 17 cm; yellow green 146D; strigose hairs, sparse, 1 mm in length, greyed purple 187A; cluster of inflorescences grows to 17 cm long and 30 cm wide.

*Leaves on flowering stem*.—Simple, linear to cuneate, grows to 8.5 cm long and 2.5 cm wide, margins serrate, base attenuate, tip acute, topside yellow green 137C, veins green 137C, bottom side green 137B.

*Size*.—Grows to 8.5 cm wide and 2 cm deep as disc enlarges.

*Form*.—Ray florets held mostly horizontally, mature disc is rounded and slightly pointed.

*Immature inflorescence*.—1.725 cm wide and 0.75 cm deep, ray florets held upright and tubular, greyed orange N170A, disc color brown 203B.

*Ray florets*.—Without pistil or stamen, ranging from 60 to 80 in number, grow to 42 mm long and 10 mm wide, with the tip two-to-three-lobed (lobes ovate with margins entire, tips acute), top side pubescent, inside glabrous; greyed purple 183A at base. Floret tip greyed orange 163A and bottom side tinted greyed green 195A.

*Disc*.—Rounded, becoming 5 mm deep and 15 mm wide with maturity, brown 200A.

*Disc florets*.—Numerous: too many to quantify, bisexual, each with 1 pistil and 5 stamen, grow to 4 mm long and 1 mm wide; corolla 3 mm long and 1 mm wide, tubular, glandular, 5 lobed, lobes triangular, brown 200A, pistil 6 mm long, greyed purple N186B, ovary 3.5 mm long, green-white 157A, style 4 mm long, greyed purple N186A, 2-branched stigma greyed purple 186C; stamen 5 mm long, greyed purple 187A; pollen, none present.

*Phyllaries*.—In 3 or 4 leafy series, area grows to 40 mm wide and 5 mm deep, lobes cuneate in shape, slightly reflexed, grow to 18 mm long and 6 mm wide, green 137C on both sides, tip acuminate, margin entire, strigose on both sides.

*Receptacle*.—Grows to 7 mm wide and 9 mm deep, white NN155A.

*Bloom period*.—June through October in Canby, Oregon.

*Fragrance*.—None.

*Lastingness*.—Each inflorescence lasts about two to three weeks in Canby, Oregon.

Seeds: 2 mm long, 0.75 mm wide, black 203B.

Disease and pests: No known resistances.

I claim:

1. A new and distinct *Rudbeckia hirta* plant named 'Summer Sienna' substantially as illustrated and described herein.

* * * * *